United States Patent
Kampe et al.

[11] 3,988,317
[45] Oct. 26, 1976

[54] HETEROCYCLIC-SUBSTITUTED NEBULARIN COMPOUNDS

[75] Inventors: Wolfgang Kampe, Heddesheim; Klaus Koch, Mannheim-Feudenheim; Kurt Stach, Mannheim-Waldhof; Harald Stork, Mannheim-Feudenheim; Felix Helmut Schmidt, Mannheim-Seckenheim, all of Germany

[73] Assignee: Boehringer Mannheim G.m.b.H., Mannheim, Germany

[22] Filed: Nov. 2, 1972

[21] Appl. No.: 303,290

[30] Foreign Application Priority Data
Nov. 17, 1971 Germany............................ 2157036

[52] U.S. Cl.................................. 536/26; 424/180
[51] Int. Cl.²......................................... C07H 19/16
[58] Field of Search .............................. 260/211.5 R

[56] References Cited
UNITED STATES PATENTS

| | | | |
|---|---|---|---|
| 3,551,409 | 12/1970 | Kampe et al................ | 260/211.5 R |
| 3,590,029 | 6/1971 | Koch et al.................... | 260/211.5 R |

*Primary Examiner*—Johnnie R. Brown
*Attorney, Agent, or Firm*—Burgess, Dinklage & Sprung

[57] ABSTRACT

New heterocyclic-substituted nebularin compounds of the formula:

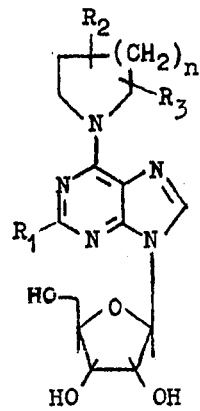

wherein
$R_1$ is hydrogen, halogen or amino;
$R_2$ and $R_3$, which may be the same or different, are hydrogen, hydroxyl, lower alkyl, alkoxy or hydroxyalkyl; and
$n$ is 2 or 3 or, when $R_1$ is a halogen atom or an amino group, $n$ can also be 1; and the pharmacologically compatible salts thereof;
are outstandingly effective in reducing body fat levels in mammals, e.g., the concentration of free fatty acids, of triglycerides and of cholesterol in serum.

15 Claims, No Drawings

HETEROCYCLIC-SUBSTITUTED NEBULARIN COMPOUNDS

The present invention is concerned with new heterocyclic-substituted nebularin compounds, with therapeutic compositions containing them, and with methods of the reducing body fat levels in mammals.

The new heterocyclic-substituted nebularin derivatives of the invention are compounds of the formula:

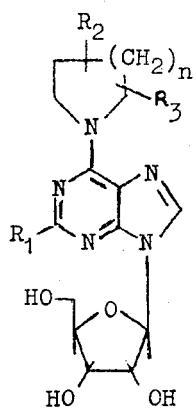

(I)

wherein
R$_1$ is hydrogen, halogen or amino;
R$_2$ and R$_3$, which may be the same or different, are hydrogen, hydroxyl, lower alkyl, alkoxy or hydroxyalkyl; and
n is 2 or 3 or, when R$_1$ is a halogen atom or an amino group, n can also be 1;
and the pharmacologically compatible salts thereof.

We have, surprisingly, found that the new compounds (I) according to the present invention do not possess the cardiac and circulatory action usual for adenosine derivatives but do exhibit an anti-lipolytic, anti-hyperlipaemic and anti-hypercholesterolaemic action. The new compounds (I) bring about a considerable reduction of the concentration of free fatty acids, of triglycerides and of cholesterol in the serum.

It is known that 6-pyrrolidino-nebularin possesses a certain cytostatic action (cf. Arzneimittelforschung, 15, 204/1965), but our investigations have shown that this compound has no action on the fat metabolism.

It is, therefore, most surprising that the compounds (I) according to the present invention are outstandingly effective in depressing body fat levels, i.e., in reducing the content of free fatty acids, triglycerides, and cholesterol in serum.

The new compounds (I) according to the present invention can be prepared, for example, by reacting a purine riboside of the general formula:

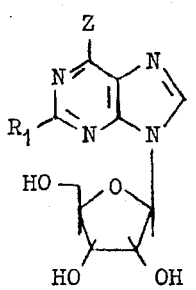

(II)

wherein R$_1$ has the same meaning as above and Z is a halogen atom or a reactive mercapto group, with an amine of the general formula:

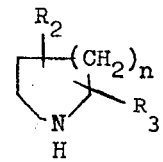

(III)

wherein R$_2$, R$_3$ and n have the same meanings as above.

If desired, the hydroxyl groups of the ribose residue can be temporarily blocked by groups which can subsequently be easily split off. Furthermore, the compounds (I) obtained can, if desired, be subsequently converted into their salts by reaction with an acid.

For carrying out the process according to the present invention, the purine riboside (II) is reacted with the amine (III) in an inert solvent, for example, n-propanol, isopropanol, butanol, tetrahydrofuran or dioxan, preferably in the presence of a tertiary amine, for example triethylamine, at ambient temperature or at a slightly elevated temperature.

As starting compounds (II), there are preferably used purine ribosides in which R$_1$ and Z are chlorine or bromine atoms, such as are described, for example, in J. Heterocyclic Chem., 1, 213/1964 and in J. Org. Chem., 31, 3262/1966. There can also be very satisfactorily used those compounds (II) in which R$_1$ is a hydrogen atom or an amino group and Z is a chlorine or bromine atom; such compounds are described, for example, in Coll. Czech. Chem. Comm., 30, 1880/1965 and in J. Org. Chem., 28, 945/1963.

If it is desired temporarily to block the hydroxyl groups of the ribose residue, then there can be used the protective groups which are conventional in sugar chemistry. For this purpose, there can be used, for example, acyl groups, preferably acetyl or benzoyl radicals, or ketals can be used, for example, the 2',3'-isopropylidene compounds, which, after the condensation reaction has taken place, can easily be converted into the free 2',3'-dihydroxyl compounds by acid hydrolysis. On the other hand, when acyl radicals are used as protective groups, they are split off by alkaline hydrolysis.

The pharmacologically compatible salts are obtained in the usual manner by neutralization of the free bases (I) with non-toxic inorganic or organic acids, for example, hydrochloric acid, sulfuric acid, phosphoric acid, hydrobromic acid, acetic acid, lactic acid, citric acid, oxalic acid, malic acid, salicylic acid, malonic acid or succinic acid.

The following Examples are given for the purpose of illustrating the invention:

EXAMPLE 1

Preparation of 6-Piperidino-nebularin 21.0 g triacetyl-6-chloro-9-(β-D-ribofuranosyl)-purine, 5.1 g piperidine and 10 ml triethylamine were heated under reflux for three hours in 200 ml isopropa-

3 nol. Subsequently, the solution was evaporated in a vacuum, the residue was taken up in chloroform and the chloroform phase was washed with water. After drying over anhydrous sodium sulfate, the solvent was distilled off. The syrupy residue was dissolved in 50 ml methanol and, after the addition of 10 ml 1N sodium methylate solution, boiled under reflux for ten minutes. The precipitate which formed upon cooling was filtered off with suction and recrystallized from about 100 ml methanol. There was obtained a total of 13.3 g (about 79% of theory) 6-piperidino-nebularin, which has a melting point of 177°–178° C.

EXAMPLE 2

Preparation of 6-(2-Methyl-piperdino)-nebularin 8.2 g triacetyl-6-chloro-9-($\beta$-D-ribofuranosyl)-purine, 3.0 g 2-methyl-piperidine and 4.5 ml. triethylamine were heated under reflux for six hours in 100 ml isopropanol. Thereafter, the solvent was distilled off in a vacuum and the residue taken up in chloroform. The chloroform solution was washed with water, dried and evaporated. The residue was dissolved in 25 ml methanol and, after the addition of 2 ml 1N sodium methylate, the solution was heated under reflux for five minutes. Subsequently, the methanol was distilled off and the residue mixed with water. The crystals which separated out upon standing in a refrigerator were filtered off with suction and recrystallized from a mixture of 25 ml each of methanol and ethyl acetate. There were obtained 3.8 g (54% of theory) 6-(2-methylpiperidino which has a melting point of 155°–157° C.

EXAMPLE 3

Preparation of 6-(2,6Dimethylpiperidino)-nebularin

A mixture of 2.86 g 6-chloro-9-($\beta$-D-ribofuranosyl)-purine and 50 ml 2.6-dimethylpiperidine was heated to 100° C for 3 hours. The reaction mixture was then evaporated in a vacuum and the residue taken up with water and ethyl acetate. The ethyl acetate phase was then dried and evaporated. The residue was recrystallized from a mixture of 25 ml ethyl acetate and 10 ml methanol, with the addition of active charcoal. There was obtained a total of 2.4 g (66% of theory) 6-(2,6-dimethylpiperidino)-nebularin, which has a melting point of 146°–148° C.

EXAMPLE 4

Preparation of 2-Amino-6-(3-methylpiperidino)-nebularin 4.3 g triacetyl-2-amino-6-chloro-9-($\beta$-D-ribofuranosyl)-purine, 1.5 g 3-methylpiperidine and 2.8 ml triethylamine were heated on a waterbath for about 6 hours in 50 ml benzene. Thereafter, the benzene phase was washed with water and evaporated. The residue was taken up in ammonia-saturated methanol and the solution left to stand overnight at ambient temperature. It was then again evaporated in a vacuum and the remaining syrup recrystallized twice from ethyl acetate. There was finally obtained 0.8 g (22% of theory) 2-amino-6-(3-methylpiperidino)-nebularin, which has a melting point of 153°–155° C and sinters at 148° C.

EXAMPLE 5

Preparation of 2-Chloro-6-pyrrolidino-nebularin 4.5 g triacetyl-2,6-dichloro-9-($\beta$-D-ribofuranosyl)-purine, 1.1 g pyrrolidine and 2.8 ml triethylamine were dissolved in 50 ml benzene. After standing for about one hour at ambient temperature, the reaction was finished. The reaction mixture was then worked up in the manner described in Example 4. After recrystallization from butanol, there were obtained 2.5 g (70% of theory) 2-chloro-6-pyrrolidino-nebularin, which has a melting point of 229° C.

EXAMPLE 6

Preparation of 2-Chloro-6-(2-methylpiperidino)-nebularin 4.5 g triacetyl-2,6-dichloro-9-($\beta$-D-ribofuranosyl)purine, 1.5 g 2-methylpiperidine and 2.8 ml triethylamine were left to stand overnight at ambient temperature in 50 ml chloroform. The chloroform phase was washed with dilute hydrochloric acid and subsequently with water and then dried and evaporated. The residue was mixed with 30 ml ammonia-saturated methanol and the solution left to stand overnight at ambient temperature. The methanol was distilled off and the residue taken up in ether and water. The ethereal phase was dried and evaporated. Since the syrupy residue did not crystallize, it was dissolved in ethyl acetate and the product precipitated out by the dropwise addition of ligroin. There were finally obtained 2.4 g (64% of theory) of chromatographically pure 2-chloro-9-(2-methyl-piperidino)-nebularin, which sinters above about 75° C.

EXAMPLE 7

Preparation of 2-Chloro-6-hexamethyleneimino-nebularin 4.5 g triacetyl-2,6-dichloro-9-($\beta$-D-ribofuranosyl)-purine, 1.5 g hexamethyleneimine and 2.8 ml triethylamine were left to stand overnight at ambient temperature in 50 ml benzene. Subsequently, the reaction mixture was worked up in a manner analogous to that described in Example 6 and purified. In this manner, there were obtained 2.9 g (76% of theory) of chromatographically pure 2-chloro-6-hexamethyleneimino-nebularin, which sinters at about 50° C.

The following compounds were obtained in an analogous manner:

a. 6-(3-methylpiperidono)-nebularin;
  m.p. 140° – 151° C; yield 54% of theory; from triacetyl-6-chloro-9-($\beta$-D-ribofuranosyl)-purine and 3-methylpiperidine;

b. 6-(4-methylpiperidino)-nebularin;
  m.p. 163° – 164° C; yield 58% of theory; from triacetyl-6-chloro-9-($\beta$-D-ribofuranosyl)-purine and 4-methylpiperidine;

c. 6-(4-methoxypiperidino)nebularin;
  m.p. 156° – 157° C; yield 34% of theory; from triacetyl-6-chloro-9-($\beta$-D-ribofuranosyl)-purine and 4-methoxypiperidine;

d. 6-[4-(2-hydroxyethyl)-piperidino]-nebularin;
  m.p. 182° – 184° C; yield 29% of theory; from triacetyl-6-chloro-9-($\beta$-D-ribofuranosyl)-purine and 4-(2-hydroxyethyl)-piperidine;

e. 6-hexamethyleneimino-nebularin;

m.p. 178° – 179° C; yield 50% of theory; from triacetyl-6-chloro-9-(β-D-ribofuranosyl)-purine and hexamethyleneimine;

f. 2-amino-6-piperidino-nebularin;

sinters above about 110° C; yield 25% of theory; from triacetyl-2-amino-6-chloro-9-(β-D-ribofuranosyl)-purine and piperidine;

g. 2-amino-6-(4-isopropoxypiperidino)-nebularin;

m.p. 123° – 125° C; yield 41% of theory; from triacetyl-2-amino-6-chloro-9-(β-D-ribofuranosyl)-purine and 4-isopropoxypiperidine;

h. 2-amino-6-pyrrolidino-nebularin;

sinters above about 80° C; yield 23% of theory; from triacetyl-2-amino-6-chloro-9-(β-D-ribofuranosyl)-purine and pyrrolidine;

i. 2-amino-6-hexamethyleneimino-nebularin;

sinters above about 70° C; yield 42% of theory; from triacetyl-2-amino-6-chloro-9-(β-D-ribofuranosyl)-purine and hexamethylene-imine;

j. 2-chloro-6-piperidino-nebularin;

sinters above about 70° C; yield 25% of theory; from triacetyl-2.6-dichloro-9-(β-D-ribofuranosyl)-purine and piperidine;

k. 2-chloro-6-(3-methyl-piperidino)-nebularin;

sinters above about 75° C; yield 86% of theory from triacetyl-2.6-dichloro-9-(β-D-ribofuranosyl)-purine and 3-methylpiperidine;

l. 2-chloro-6-(4-methylpiperidino)-nebularin;

sinters above about 85° C; yield 73% of theory; from triacetyl-2.6-dichloro-9-(β-D-ribofuranosyl)-purine and 4-methyl-piperidine;

m. 2-chloro-6-(2.6-dimethylpiperidino)-nebularin;

sinters above about 80° C; yield 38% of theory; from triacetyl-2.6-dichloro-9-(β-D-ribofuranosyl)-purine and 2.6-dimethyl-piperidine;

n. 6-(4-hydroxypiperidino)-nebularin;

m.p. 220° – 222° C; yield 68% of theory; from 6-chloro-9-(β-D-ribofuranosyl)-purine and 4-hydroxypiperdine;

o. 2-chloro-6-(4-hydroxypiperidino)-nebularin;

sinters from about 70° C; yield 73% of theory; from triacetyl-2.6-dichloro-9-(β-D-ribofuranosyl)-purine and 4-hydroxypiperidine.

The compounds of this invention are, as indicated above, useful to decrease serum lipids in mammals.

The effectiveness of the instant compounds on the lowering of free fatty acids in the blood serum was determined as follows. The procedure was carried out using for each compound ten healthy male Sprague-Dawley rats, each weighing about 200 g. The animals were kept without food for 16 to 18 hours before application. The compounds were administered either p.o., with a stomach tube, suspended in tylose or intraperitoneally (i.p.) in an aqueous buffered solution. The control group in each instance received only the solvent in the same manner of application. One hour after application of the compounds (or of the solvent alone for establishing the control values) the animals were killed and exsanguinated and the triglycerides from the serum were determined in accordance with the method of KREUTZ and EGGSTEIN as modified by SCHMIDT et al (Z. klin. Chem. u.klin. Biochem., 6 Jhrg., 1968, pages 156 – 159).

The results are set forth in the following Table 1, expressed as percentage reduction of the triglycerides in the serum of treated animals relative to the control animals.

TABLE 1

| Compound No. (Preparative Example No.) | | Test Compound | Dosage (mg/kg) | Application Method | Fat Depression (in %) |
|---|---|---|---|---|---|
| 1 | (Ex. 1) | 6-piperidino-nebularin | 0.5 | i.p. | 60 |
| 2 | (Ex. 1) | 6-piperidino-nebularin | 1.0 | p.o. | 30 |
| 3 | (Ex. 5) | 2-chloro-6-pyrrolidino-nebularin | 0.5 | i.p. | 34 |
| 4 | (Ex. 6) | 2-chloro-6-(2-methylpiperidino)-nebularin | 0.5 | i.p. | 34 |
| 5 | (Ex. 7, 1st listing) | 2-chloro-6-hexamethylenimino-nebularin | 0.5 | i.p. | 31 |
| 6 | (Ex. 2) | 6-(2-methylpiperidino)-nebularin | 0.5 | i.p. | 42 |
| 7 | (Ex. 4) | 2-Amino-6-(3-methylpiperidino)-nebularin | 0.5 | i.p. | 19 |
| 8 | (Ex. 7, 2nd listing) | 6-(3-methylpiperidino)-nebularin | 0.5 | i.p. | 26 |
| 9 | (Ex. 7, 9th listing) | 2-amino-6-pyrrolidino-nebularin | 0.5 | i.p. | 15 |
| 10 | (Ex. 7, 6th listing) | 6-hexamethylenimino-nebularin | 0.5 | i.p. | 12 |
| 11 | (Ex. 7, 16th listing) | 2-chloro-6-(4-hydroxypiperidino)-nebularin | 0.5 | i.p. | 11 |
| 12 | (Ex. 7, 11th listing) | 2-chloro-6-piperidino-nebularin | 0.5 | i.p. | 28 |
| 13 | (Ex. 7, 7th listing) | 2-amino-6-piperidino-nebularin | 0.5 | i.p. | 20 |
| A | | 6-pyrrolidino-nebularin (Comparison Compound)* | 0.5 | i.p. | 0 |

*Disclosed in "Arzneimittelforsch." 15 (1965), page 204.

The data in Table 1 show a substantially better effectiveness of the new compounds as compared with the known compound, 6-pyrrolidino-nebularin, in that much less of the new compounds is required to induce the same result.

As previously indicated, the nebularin derivatives of this invention are readily adapted to therapeutic use as cardio and fat-affecting agents. The toxicity of the compounds of the invention has been found to be quite low or substantially non-existent when they are administered in amounts that are sufficient to achieve the desired therapeutic effects. Moreover, no other pharmacological side effects have been observed to occur as a result of their administration.

In accordance with the method of treatment of the present invention, the compounds can be given via the oral route. However, the compounds can also be administered as parentarals in the form of their solutions or suspensions. The compounds can be administered either alone and/or preferably in combination with a pharmaceutically acceptable carrier, and such administration can be carried out in both single and multiple dosages. More particularly, the compounds of this invention can be administered in a wide variety of different dosage forms wherein they are combined with various pharmaceutically acceptable inert carriers in the form of tablets, capsules, dragees, powders, aqueous suspensions, solutions, and the like. Such carriers include solid diluents or fillers, liquid aqueous media and various non-toxic organic solvents, etc. In general, the therapeutically effective compounds are present in such dosage forms at concentration levels ranging from about 0.01 to about 90% by weight of the total composition, i.e. in amounts which are sufficient to provide the desired unit dosage, to total, e.g., from 0.001 to 5 mg/kg per day.

In dosage unit form, the compounds as set out herein are used in amounts of from 0.1 to 50 mg active ingredients per dosage unit. Preferably, the compositions are compounded so that for parenteral administration, 0.5 − 5 mg active compound/dosage unit is present and for oral administration 2 − 10 mg. of compound/dosage unit.

As pharmaceutical compositions according to the present invention, there can be used all the conventional oral or parenteral forms of administration, for example, tablets, capsules, dragees, syrups, solutions, suspensions, drops, suppositories and the like. For this purpose, the active material is mixed with solid or liquid carrier materials and the mixture subsequently brought into the desired form. Examples of solid carrier materials include lactose, mannitol, starch, talc, methyl-cellulose, silicic acid, calcium phosphate, magnesium stearate, agar-agar and gelatine to which, if desired, can be added coloring materials and flavorings. Liquid carrier materials for injection solutions must, of course, be sterile and are preferably packed into ampoules.

It will be understood that the specification and examples are illustrative but not limitative of the present invention and that other embodiments within the spirit and scope of the invention will suggest themselves to those skilled in the art.

What is claimed is:
1. Nebularin compounds of the formula:

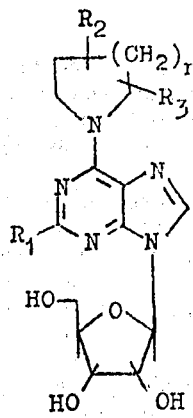

wherein $R_1$ is hydrogen, halogen or amino;
$R_2$ and $R_3$, which may be the same or different, are hydrogen, hydroxyl, lower alkyl, lower alkoxy or lower hydroxyalkyl; and
n is 2 or 3 or, when $R_1$ is a halogen atom or an amino group, n can also be 1; and the pharmacologically compatible salts thereof.

2. Compound as claimed in claim 1 wherein $R_1$ in the formula is hydrogen.

3. Compound as claimed in claim 1 wherein $R_1$ in the formula is halogen.

4. Compound as claimed in claim 1 wherein $R_1$ in the formula is amino.

5. Compound as claimed in claim 1 wherein at least one of $R_2$ and $R_3$ is hydrogen.

6. Compound as claimed in claim 1 wherein at least one of $R_2$ and $R_3$ is hydroxyl.

7. Compound as claimed in claim 1 wherein at least one of $R_2$ and $R_3$ is lower alkyl, lower alkoxy, or lower hydroxyalkyl of from 1 to 6 carbon atoms.

8. Compound as claimed in claim 1 wherein $R_1$ is hydrogen and n is 2 and 3.

9. Compound as claimed in claim 1 wherein $R_1$ is halogen or amino and n is 2 or 3.

10. Compound as claimed in claim 1 wherein $R_1$ is halogen or amino and n is 1.

11. Compound as claimed in claim 1 designated 6-piperidino-nebularin.

12. Compound as claimed in claim 1 designated 2-chloro-6-pyrrolidino-nebularin.

13. Compound as claimed in claim 1 designated 2-chloro-6-(2-methylpiperidino)-nebularin.

14. Compound as claimed in claim 1 designated 2-chloro-6-hexamethyleneimino-nebularin.

15. A compound of the formula:

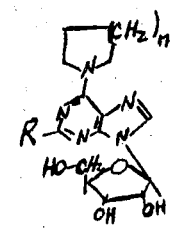

wherein R is hydrogen or amino and n is 2 or 3.